United States Patent

Nakata et al.

Patent Number: 5,906,927
Date of Patent: May 25, 1999

[54] PROCESS FOR PRODUCING L-2-AMINOADIPIC ACID

[75] Inventors: Kuniho Nakata; Takao Narita; Hiroshi Tsunekawa, all of Fujisawa; Takeo Yoshioka, Ayase, all of Japan

[73] Assignees: Mercian Corporation; Chugai Seiyaku Kabushiki Kaisha, both of Tokyo, Japan

[21] Appl. No.: 08/913,722

[22] PCT Filed: Apr. 3, 1996

[86] PCT No.: PCT/JP96/00913

§ 371 Date: Sep. 22, 1997

§ 102(e) Date: Sep. 22, 1997

[87] PCT Pub. No.: WO96/31616

PCT Pub. Date: Oct. 10, 1996

[30] Foreign Application Priority Data

Apr. 7, 1995 [JP] Japan .................................. 7-081626

[51] Int. Cl.⁶ .............................. C12P 13/04; C12N 1/20
[52] U.S. Cl. ............................................ 435/106; 435/850
[58] Field of Search ..................................... 435/106, 850

[56] References Cited

PUBLICATIONS

Kenji Soda et al, "L–Lysine—α–Ketoglutarate Aminotransferase. I. Identification of a Product, $\Delta^1$ – Piperideine –6–carboxylic Acid", Biochemistry, 7(11)4102–4109, 1968.

Soda et al, "L–Lysine—α–Ketoglutarate Aminotransferase. II. Purification, Crystallization, and Properties", Biochemistry, 7(11)4110–4119, 1968.

Soda et al, "Studies on Transamination in Microorganisms, Part III. L–Lysine—α–Ketoglutarate Acid Transaminase Reaction", Agr. Biol. Chem., 25(11)811–819, 1961.

APS Abstract of Japanese Patent 06–181787 Nakayama, Jul. 5, 1994.

APS Abstract of Japanese Patent 60–160889 Yokozeki et al, Aug. 22, 1985.

Biosis Abstract 80:247113 Kern et al "Antimicrob Agents Chemother" 17(4) 1980 pp. 679–685, 1980.

*Primary Examiner*—Herbert J. Lilling
*Attorney, Agent, or Firm*—Burns, Doane, Swecker & Mathis, LLP

[57] ABSTRACT

A process for producing L-2-aminoadipic acid, which comprises converting an aminomethyl group of L-lysine into a carboxyl group by use of a culture of a microorganism of the genus Flavobacterium. By this process, L-2-aminoadipic acid can be obtained directly from L-lysine in a high yield. This process is a microbial method which is effective for the mass production.

7 Claims, No Drawings

PROCESS FOR PRODUCING L-2-AMINOADIPIC ACID

TECHNICAL FIELD

The present invention relates to a process for producing L-2-aminoadipic acid by utilizing microorganisms. L-2-Aminoadipic acid is a nonprotein amino acid and it is usable as a valuable intermediate for medicines such as a methotrexate derivative (WO 92/09436) effective as an antirheumatic drug, remedy for psoriasis and carcinostatic agent. This compound is also usable as a terminal-modifying agent for physiologically active peptides such as peptide antibiotics and peptide hormones and as a precursor in the fermentative production of β-lactam antibiotics typified by penicillins and cephalosporins.

BACKGROUND OF THE INVENTION

L-2-Aminoadipic acid is found widely in the biological field including Cholera vibrio which is a bacterium, vegetables typified by corns and frog embryos. Further, L-2-aminoadipic acid also holds a position of an intermediate in the biosynthesis of lysine with eukaryotic microorganisms or of a precursor in the biosynthesis of β-lactam antibiotics. The chemical synthesis of L-2-aminoadipic acid is not yet an effective means from the viewpoint of the cost, since an optical resolution and multi-stage reactions are necessitated. As for the production of L-2-aminoadipic acid with microorganisms, a process wherein this acid is produced from L-pipecolic acid with a microorganism of Alcaligenes, Pseudomonas or Kurthia [Japanese Patent Unexamined Published Application (hereinafter referred to as "J. P. KOKAI") No. Hei 1-98495] and there is also known a process wherein it is produced from L-lysine with a microorganism of Agrobacterium, Klebsiella, Alcaligenes, Brevibacterium or Bacillus (J. P. KOKAI No. Hei 6-181787). However, these two processes have problems when they are to be employed for the mass production. Namely, starting L-pipecolic acid is expensive in the former process and the reaction efficiency is usually low in the latter process.

DISCLOSURE OF THE INVENTION

The object of the present invention is to provide a microbial process for the mass production L-2-aminoadipic acid directly from L-lysine in a high yield.

The present invention has been completed on the basis of a finding that L-2-aminoadipic acid can be directly and efficiently obtained from L-lysine by using a microorganism of a specified genus capable of converting an aminomethyl group into carboxyl group by the oxidation without modifying the α-amino group of the lysine.

Namely, the present invention provides a process for producing L-2-aminoadipic acid, which comprises the step of converting an aminomethyl group of L-lysine into a carboxyl group by use of a culture of a microorganism of the genus Flavobacterium.

BEST MODE FOR CARRYING OUT THE INVENTION

L-2-Aminoadipic acid produced by the process of the present invention is represented by the following formula 1:

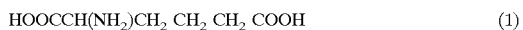

HOOCCH(NH$_2$)CH$_2$ CH$_2$ CH$_2$ COOH           (1)

The products of the present invention also include salts of the compound described above.

The salts include salts of L-2-aminoadipic acid with organic acids such as acetic acid and tartaric acid; inorganic acids such as hydrochloric acid and sulfuric acid; organic bases such as triethylamine and N-methylmorpholine; and inorganic bases such as sodium hydroxide and potassium hydroxide.

The microorganism of the genus Flavobacterium usable in the present invention may be that of any strain of the genus Flavobacterium so far as it is capable of converting the aminomethyl group of lysine into carboxyl group by the oxidation to directly form L-2-aminoadipic acid from lysine. A preferred example thereof is a bacterium of No. 7-1 strain of the genus Flavobacterium which is obtained from the soil. The No. 7-1 strain is deposited with the National Institute of Bioscience and Human-Technology Agency of Industrial Science and Technology, the Ministry of International Trade and Industry (address: 1-3, Higashi 1-chome, Tsukuba-shi, Ibaraki-ken, Japan) under FERM BP-5457 (Flavobacterium sp. 7-1; deposition date: Jan. 17, 1995).

The No. 7-1 strain is a gram-negative, aerobic bacillus having a cell width of 0.5 μm and length of 2 μm, which forms no endospores and which is positive to catalase, oxidase and phosphatase and secretes a yellow pigment. This strain is free from flagella and has no motility. From these physiological properties, the strain was identified with that of the genus Flavobacterium according to Bergey's Manual of Systematic Bacteriology.

The medium for culturing the microorganism is not particularly limited and any of media usually used for the culture of microorganisms is usable.

For example, as the carbon source, any of those which can be utilized by the above-described microorganism is usable. In particular, the carbon sources usable herein include saccharides such as glucose, fructose, sucrose and dextrin; sugar alcohols such as glycerol and sorbitol; and organic acids such as fumaric acid and citric acid. Usually, these carbon sources are added to the medium desirably in an amount of about 0.1 to 10% by weight (hereinafter referred to as "%").

The nitrogen sources usable herein include ammonium salts of inorganic acids such as ammonium chloride, ammonium sulfate and ammonium phosphate; ammonium salts of organic acids such as ammonium fumarate and ammonium citrate; and natural nitrogen sources such as a meat extract, yeast extract, corn steep liquor and casein hydrolyzate. Usually, these nitrogen sources are added to the medium in an amount of desirably about 0.1 to 10% by weight.

The inorganic salts usable herein include alkali metal phosphates such as potassium phosphate and sodium phosphate; alkali metal chlorides such as potassium chloride and sodium chloride; and metal sulfates such as magnesium sulfate and ferrous sulfate. Usually, these inorganic salts are added to the medium in an amount of desirably about 0.001 to 1% by weight.

A liquid culture with an ordinary growth medium for bacteria is preferred. Particularly effective carbon sources are glucose, maltose, starch, etc., and particularly effective nitrogen sources are ammonium sulfate, peptone, yeast extract, soybean powder, etc. In addition, potassium phosphate, magnesium sulfate, common salt, etc. are usually used as the inorganic salts.

The microorganism may be cultured in the above-described medium at 20 to 40° C., preferably 28 to 37° C. and at a pH of 5 to 9, preferably 6 to 8 under aerobic conditions.

The cultures of the microorganism utilizable in the present invention include the whole culture medium, cells, culture filtrate and products obtained by treating them. The products obtained by treating the cells include the dry cells, cells treated with an organic solvent such as acetone, toluene or methanol, cell extracts, and immobilized cells. The products obtained by treating the culture filtrate include a concentrate thereof and dry powder. Further, the enzyme separated from the cultured cells and culture filtrate are usable after the purification.

The present invention can be conducted by inoculating the medium with the microorganism, culturing the microorganism at, for example, 20 to 40° C. for 12 to 120 hours to obtain a strain culture liquid containing $10^6$ to $10^{10}$ cells/ml, adding L-lysine as the starting compound to the culture liquid directly or after dissolving L-lysine in water or an assistant solvent so as to adjust the final concentration to 0.5 to 30 mg/ml, conducting the reaction usually at 20 to 40° C. for 18 hours to 7 days, preferably 18 hours to 5 days, and purifying the product by an ion exchange chromatography with a cation exchange resin, anion exchange resin or the like, adsorption chromatography of, for example, HP 20, or precipitation or crystallization, taking advantage of the difference of solubility in the solvent and temperature to obtain L-2-aminoadipic acid.

Although the form of L-lysine to be added or the time of the addition thereof are not particularly limited, it is preferred to use L-lysine in the form of its monohydrochloride from the viewpoint of the solubility or the like, and L-lysine may be added at the start of the culture or at any time in the period of the first to the fifth day of the culture.

According to the present invention, L-2-aminoadipic acid usable as a valuable intermediate for a methotrexate derivative (WO 92/09436) useful as an antirheumatic drug, remedy for psoriasis and carcinostatic agent can be directly and efficiently produced from L-lysine or a salt thereof by a simple operation.

The following Examples will further illustrate the present invention, which by no means limit the invention.

EXAMPLE 1

A 300 ml flask containing 30 ml of a liquid medium comprising 3.7% Brain Heart Infusion was sterilized, and 1/10 of 20% L-lysine monohydrochloride solution (adjusted to pH 8.0 with sodium hydroxide) was fed into the flask. After the inoculation of No. 7-1 strain cultured by slant culture, the shaking culture was conducted at 220 rpm at 28° C. for 96 hours. The supernatant liquid was taken by the centrifugation, and L-2-aminoadipic acid contained in the supernatant liquid was determined by the liquid chromatography and thin-layer chromatography described below to find that 5.0 g/l of L-2-aminoadipic acid was produced.

Liquid-Chromatographic Method
  Column: Shim-pack ISC-07/S1504
  Mobile phase:
    liquid A: 0.2 N sodium citrate (pH 3.2) 7% ethanol
    liquid B: 0.6 N sodium citrate (pH 10.0)
    liquid C: 0.2 N sodium hydroxide
    Gradient elution
  Flow rate: 0.3 ml/min
  Temperature: 55° C.
  Detector: Fluorescent detector (Ex 348 nm, Em 460 nm)
  Reagent:
    liquid a: 0.04% sodium hypochlorite
      carbonate/borate buffer solution
    liquid b: 0.08% o-phthalaldehyde
      0.1% N-acetylcysteine
      carbonate/borate buffer solution Flow rate of reagent: both liquids a and b: 0.2 ml/min
Thin-Layer Chromatographic Method
  Thin layer: silica gel thin layer 1.05715 (a product of Merck)
  Developer: n-butanol / acetic acid / water=3/1/1
  Coloring: ninhydrin According to the following liquid chromatographic analysis, it was confirmed that 2-aminoadipic acid thus obtained comprised 100% L-type compound:
  Column: CROWNPAK CR (+) (a product of Daicel Chemical Industries, Ltd.)
  Mobile phase: aqueous perchloric acid solution having pH of 2.0
  Detection: differential refractometer

EXAMPLE 2

A 500 ml flask containing 150 ml of a medium comprising 3% of maltose, 1% of bactopeptone, 0.5% of yeast extract, 0.1% of dipotassium phosphate, 0.05% of magnesium sulfate and 0.8% of sodium chloride (pH 6.8) was sterilized. After the inoculation of No. 7-1 strain, the shaking culture was conducted at 220 rpm at 28° C. for 24 hours. The culture liquid was charged into a 30 l jar fermenter containing 15 l of the medium. 300 g of L-lysine hydrochloride and 0.75 g of Adekanol (an antifoaming agent; a product of Asahi Denka Kogyo K.K.) were added to the jar medium. After conducting the culture under the aeration and stirring for 5 days, 90 g of L-2-aminoadipic acid was formed.

After the addition of Perlite, the culture liquid was filtered. The filtrate was concentrated to a volume of 1/10 with a rotary evaporator. The pH of the concentrate was adjusted to 3.2 with hydrochloric acid, and the concentrate was cooled to 4° C. The precipitate thus formed was taken by the filtration and dissolved in ion-exchanged water to obtain a 2% solution. The pH of the solution was adjusted to 10 with ammonia. After the adsorption with 7.9 l of an anion exchange resin IRA-402 (AcO⁻ type) followed by the washing with water, the product was subjected to the fractional elution with 0.5 N acetic acid. After the concentration followed by the cooling to 4° C., the obtained crystals were dried to obtain 82 g of L-2-aminoadipic acid in the form of a white powder.

We claim:

1. A process for producing L-2aminoadipic acid which comprises the step of converting an aminomethyl group of L-lysine into a carboxyl group by use of a culture of a microorganism of the genus Flavobacterium, wherein said microorganism is Flavobacterium sp 7-1 strain (FERM BP-5457).

2. A process for producing L-2-aminoadipic acid which comprises the step of converting an aminomethyl group of L-lysine into a carboxyl group by use of a culture of a microorganism of the genus Flavobacterium, wherein L-lysine is added to the culture of a microorganism of the genus Flavobacterium, the microorganism is cultured at 20 to 40° C. for 18 hours to 7 days and L-2-aminoadipic acid thus obtained is isolated.

3. The process according to claim 2, wherein the culture of the microorganism of the genus Flavobacterium is one obtained by inoculating a liquid medium with a microorganism of the genus Flavobacterium and culturing the microorganism at 20 to 40° C. for 12 to 120 hours.

4. The process according to claim 2, wherein L-lysine is added so that its concentration is 0.5 to 30 mg/ml.

5. The process according to claim 2, wherein the culture is conducted at a pH of 5 to 9 under aerobic conditions after the addition of L-lysine.

6. A process for producing L-2-aminoadipic acid which comprises the steps of inoculating a liquid medium with a microorganism of the genus Flavobacterium, culturing the microorganism at 20 to 40° C. for 12 to 120 hours, then adding L-lysine to the thus-obtained mixture, conducting the culture at a pH of 5 to 9 at 20 to 40° C. under aerobic conditions for 18 hours to 7 days and isolating L-2-aminoadipic acid thus formed.

7. The process according to claim 6, wherein the microorganism of the genus Flavobacterium is Flavobacterium sp 7-1 strain (FERM BP-5457).

* * * * *